United States Patent [19]
Moore

[11] Patent Number: 6,053,916
[45] Date of Patent: Apr. 25, 2000

[54] SACROILIAC IMPLANT

[76] Inventor: Michael R. Moore, 7199 S. Chapparal Cir. West, Aurora, Colo. 80116

[21] Appl. No.: 09/251,392

[22] Filed: Feb. 17, 1999

[51] Int. Cl.⁷ .................................................. A61B 17/56
[52] U.S. Cl. ............................... 606/61; 606/72; 606/73; 623/17
[58] Field of Search ................................. 606/61, 72, 73; 623/17; 411/413

[56] References Cited

U.S. PATENT DOCUMENTS

| | | | |
|---|---|---|---|
| 4,175,555 | 11/1979 | Herbert | 129/92 B |
| 4,328,593 | 5/1982 | Sutter et al. | 3/1.91 |
| 4,501,269 | 2/1985 | Bagby | 128/92 |
| 4,653,486 | 3/1987 | Coker | 128/92 YF |
| 4,936,848 | 6/1990 | Bagby | 623/17 |
| 5,015,247 | 5/1991 | Michelson | 606/61 |
| 5,019,079 | 5/1991 | Ross | 606/72 |
| 5,458,638 | 10/1995 | Kuslich et al. | 623/17 |
| 5,591,235 | 1/1997 | Kuslich | 623/17 |
| 5,702,453 | 12/1997 | Rabbe et al. | 623/17 |
| 5,702,455 | 12/1997 | Saggar | 623/17 |
| 5,709,683 | 1/1998 | Bagby | 606/61 |
| 5,766,253 | 6/1998 | Brosnahan, III | 623/17 |
| 5,776,197 | 7/1998 | Rabbe et al. | 623/17 |
| 5,776,198 | 7/1998 | Rabbe et al. | 623/17 |
| 6,001,101 | 12/1999 | Augagneur et al. | 606/73 |

FOREIGN PATENT DOCUMENTS

| | | |
|---|---|---|
| 567424 | 10/1993 | European Pat. Off. . |
| 43-02-397 | 7/1993 | Germany . |

OTHER PUBLICATIONS

"BAK™ Interbody Fusion System", *Patient Guide* brochure, Feb., 1998.
"Herbert/Whipple™ Bone Screw System," brochure, Zimmer, Feb., 1992.
"The Herbert Bone Screw System", *Fracture Management*, Zimmer, Rev. Mar. 1987.
Hansen A. Yuan, MD, et al., "Prospective Multi–Center Clinical Trial of the BAK™ Interbody Fusion System", pp. 1–8.

*Primary Examiner*—Michael Buiz
*Assistant Examiner*—Julian W. Woo
*Attorney, Agent, or Firm*—Fields and Johnson, P.C.

[57] ABSTRACT

An implant is provided which facilitates enhanced structural stability across a joint to be immobilized. The sacroiliac implant is an elongate structure having two cylindrical sections of differing diameters. The implant further has like-handed, but dissimilar pitched threaded sections at the proximal and distal ends thereof to produce compressive forces across the joint. A hollow core traverses the length of the implant. A plurality of apertures or openings are formed through the implant transversely to the longitudinal axis and communicate with the hollow core. Bone graft or a BMP-soaked carrier fill the hollow core. The openings or apertures provide a conductive path of healing for bony ingrowth. The proximal end of the implant provides for engagement with a tool to drive the implant.

19 Claims, 4 Drawing Sheets

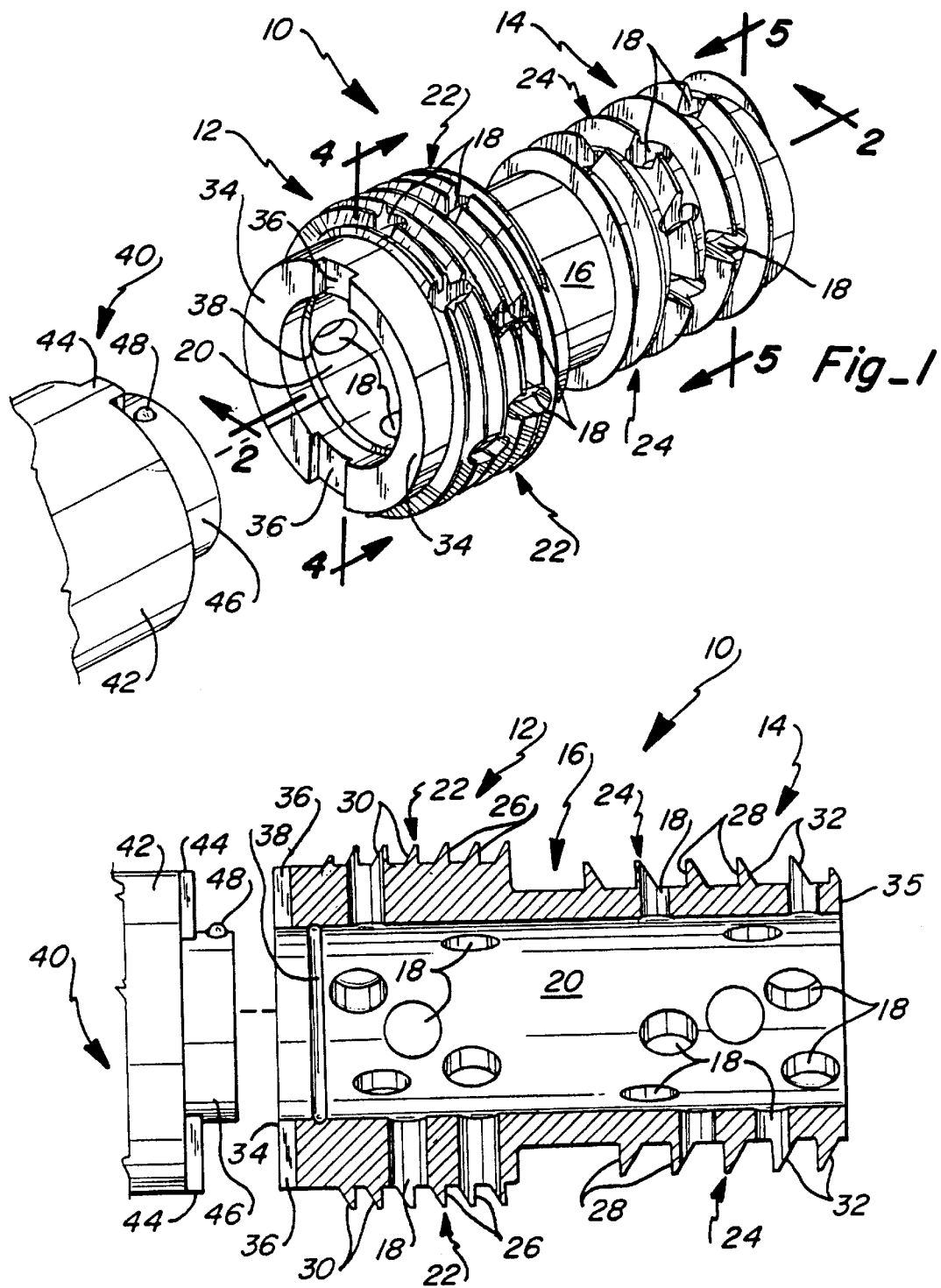

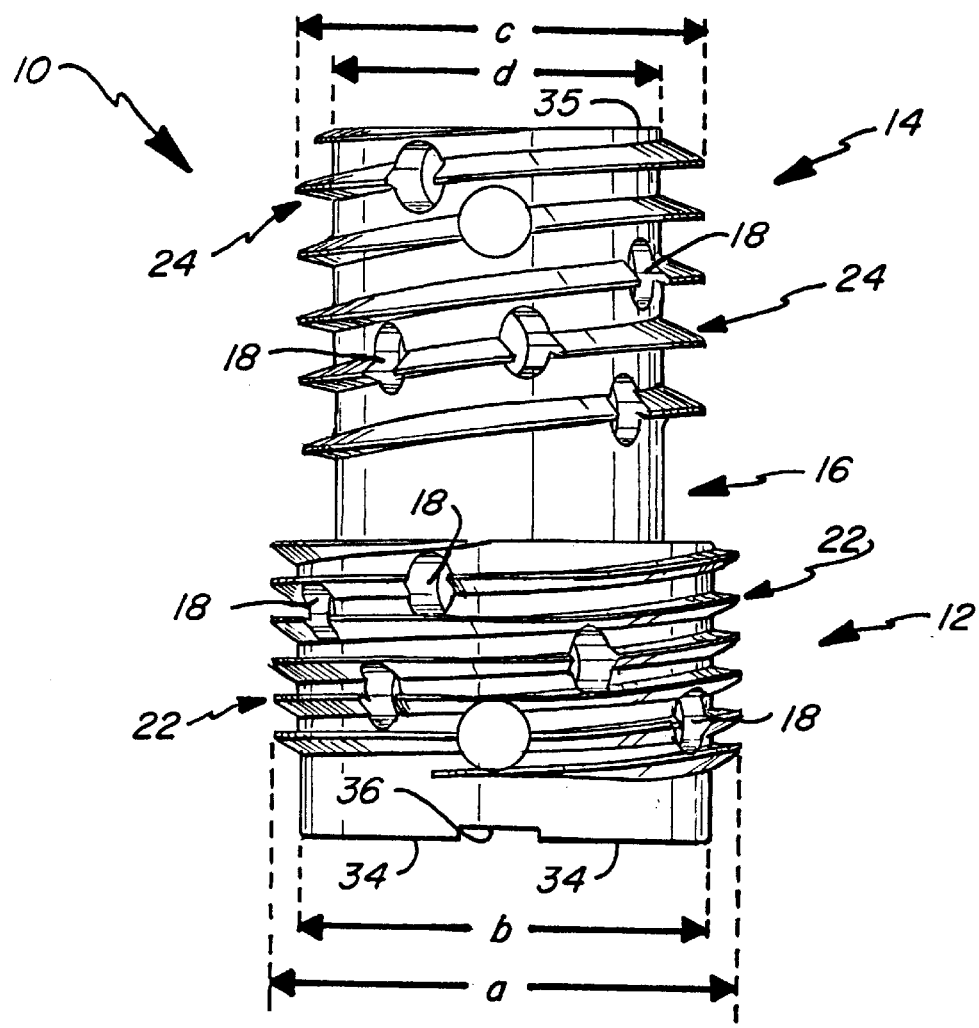
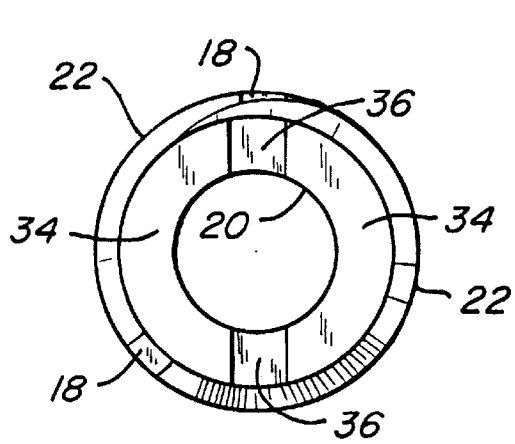 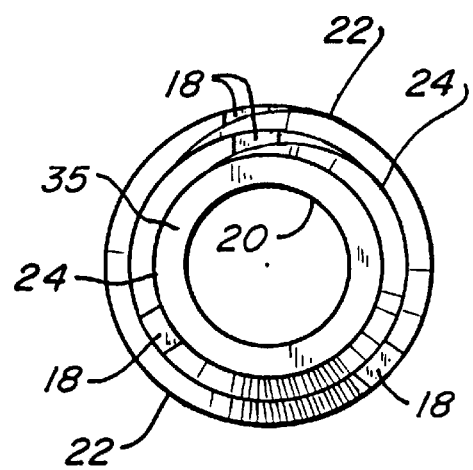
Fig_3
Fig_4  Fig_5

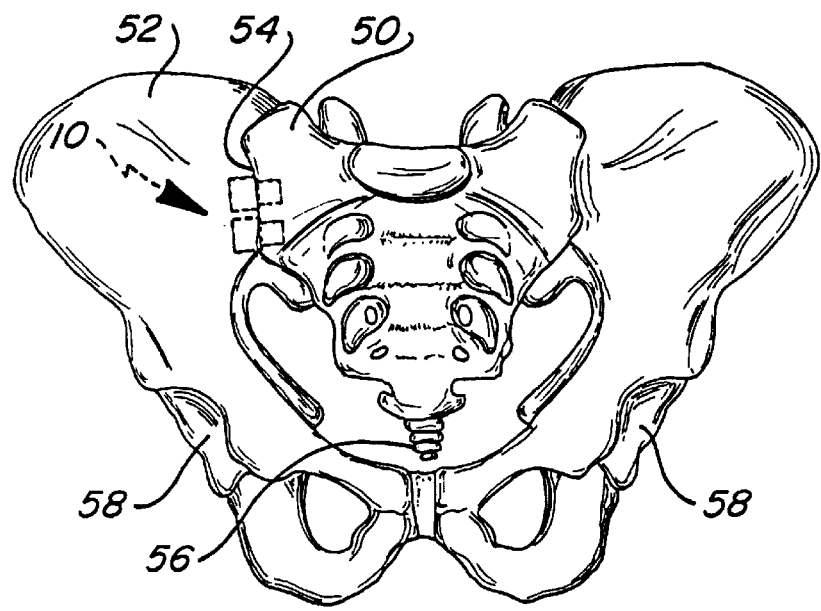
Fig_6
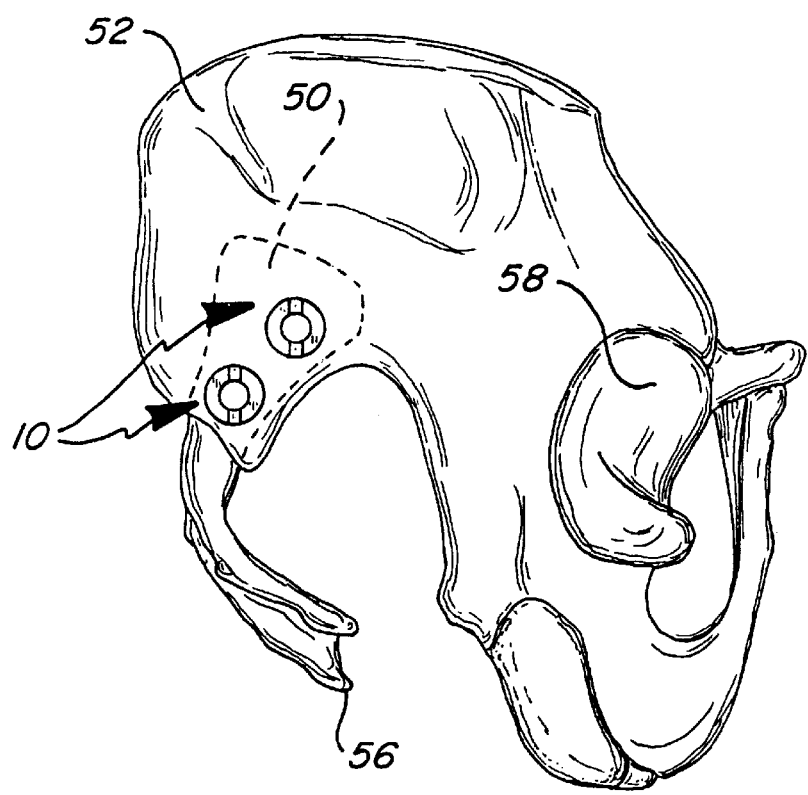
Fig_7

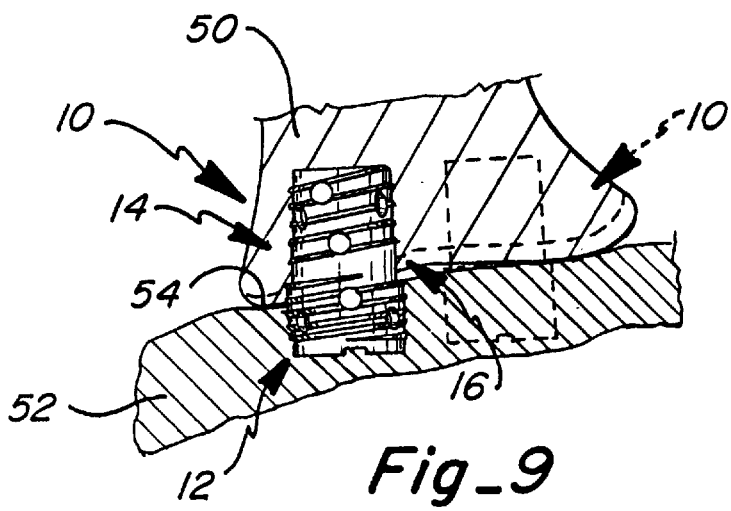
Fig_9
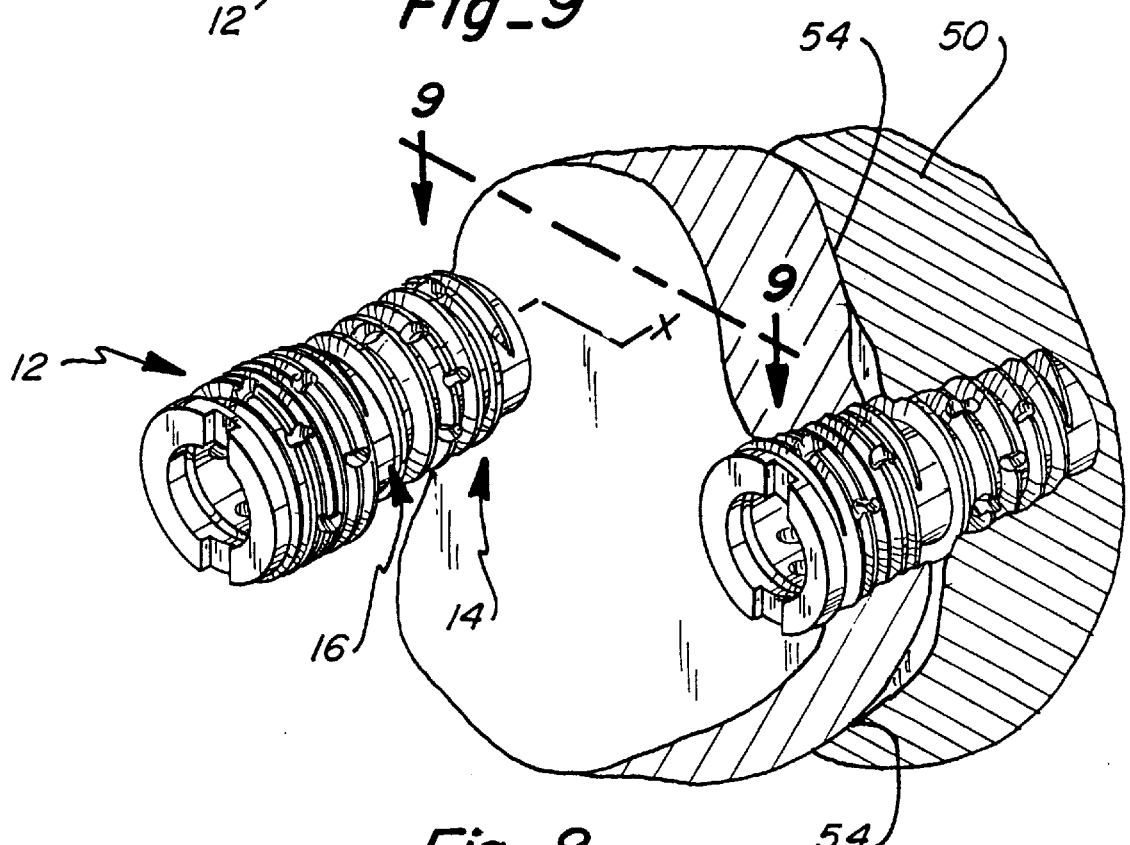
Fig_8

SACROILIAC IMPLANT

TECHNICAL FIELD

This invention relates to a bone implant and, more particularly, to a sacroiliac implant which provides stability and compression for immobilization of a joint, and facilitates bony ingrowth to further stabilize the joint by fusion.

BACKGROUND ART

A number of prior art devices exist which may be used to stabilize or fuse bones. One major group of these devices is known in the art as bone screws. Typically, bone screws are used to stabilize fractures of small bones in the body, such as those found in the hands or feet. Once implanted, these screws are completely contained within the bone which is particularly necessary in those circumstances where a protruding bone screw would otherwise damage a nearby joint.

Representative examples of a common bone screw include those disclosed in U.S. Pat. No. 4,175,555 to Herbert. The bone screw of this reference is known as a "Herbert" screw and is characterized by a shaft with screw threads on the leading and trailing ends thereof. The threads are like handed, but of different pitch. In the case of a fracture where it is necessary to join a remote bone fragment back to the major bone structure, the thread pitch of the leading end slightly exceeds that of the trailing end which causes the bones to be brought together in compression as the bone screw is screwed into place. Compression is desirable both for fracture healing and stability. Conversely, in some situations, it may be necessary to apply distraction between two bone fragments. Accordingly, the pitch of the trailing end thread may be made greater than that of the leading end. A cannula or lumen may be formed through the shaft to accommodate a guide wire to guide the bone screw to the proper location.

Another example of a bone screw is U.S. Pat. No. 5,019,079 to Ross. Like the Herbert screw, the purpose of this bone screw is also for stabilization of a fracture by providing two sets of threads which place the bones in compression. A modified intermediate or middle section is disclosed which is explained as providing better lateral stability for the joined bone structures.

Another group of devices generally known as fusion cages are used to achieve fusion between two adjacent vertebral bodies. The purpose and functioning of these fusion cages are quite different from those of bone screws. One example of a prior art spinal fusion cage is U.S. Pat. No. 5,015,247 to Michaelson. This device is characterized by a generally cylindrical or tubular member having a series of macro-sized openings which communicate with a hollow core, and a series of uniform threads extending the length of the cage. In order to achieve fusion between two vertebrae, the fusion cage must be sized so that it is wider than the disc which normally spans between the adjacent vertebral bodies, and which has an area for contacting the adjacent vertebral bodies. The threads on the cage are not for purposes of compression or distraction between two vertebrae, but rather are used for securing the cage at diametrically opposed sides with the adjacent vertebrae. The cage may be filled with bone graft and the macro-sized openings provide pathways by which bony ingrowth may occur. Eventually, a patient's body incorporates the bone graft and the fusion cage becomes structurally united with the joined vertebrae. The threads used on fusion cages must be uniform throughout the length of the cage so that the cage is advanced through the adjacent vertebrae uniformly. Unlike a bone screw, if threads of differing pitches were used on the fusion cage, the trailing set of threads would destroy the bone grooves previously filled by the forward advancing threads. Accordingly, the surrounding bone would be destroyed and the threads would actually detract from securing the adjacent vertebrae.

Another example of a fusion cage is disclosed in U.S. Pat. No. 5,766,253 to Brosnahan, III. As with the Michaelson patent, this patent also discloses a generally cylindrical cage with uniform threads extending the length of the device. In order to achieve bony ingrowth for this cage, two indentations are formed on the outer surface of the cage and the indentations are filled with bone graft. The cage is then positioned in contact with end plates of the adjacent vertebrae.

As can be seen from a review of these prior art references, a bone screw spans transversely across a gap between two bone structures, such as caused by a bone fracture, and the bone screw is used to compress or distract the two bones. A fusion cage, on the other hand, extends longitudinally along the gap between two vertebral bodies which is normally filled by a disc, and the cage is used like a spacer to replace the disc. Therefore, these devices are used for quite different purposes and are implemented at 90° from one another with respect to a gap between two opposing bone structures.

Until recently, many complaints of lower back pain and leg pain have been attributed to herniated discs or other injuries to the spinal column. Extensive therapy and treatment has often been unsuccessful in alleviating such pain. It has been recently found that some of this lower back and leg pain can be attributed to symptomatic sacroiliac dysfunction or instability. Normally, the sacroiliac joint which spans between the sacrum bone and ilium bone has nutation of one to two degrees. "Nutation" is the medical term which describes the relative movement between the sacrum and ilium. A patient's sacroiliac joint can become damaged resulting in hypermobility of the joint. Because of the small range of motion in the sacroiliac joint, hypermobility is very difficult to diagnose. Therefore, lower back pain or leg pain caused by sacroiliac dysfunction often goes misdiagnosed or undiagnosed.

Accordingly, it is one general objective of this invention to provide a device for correcting symptomatic sacroiliac dysfunction or instability. It is another general object of this invention to provide a device which enhances stability and compression for purposes of immobilizing a joint, and for fusing two opposed bone structures across the joint.

DISCLOSURE OF THE INVENTION

In accordance with the present invention, a sacroiliac implant is provided to treat health problems associated with sacroiliac dysfunction or instability. The primary purpose of the implant is to eliminate motion across the sacroiliac joint which, in turn, ameliorates hypermobility. In order to provide successful treatment for such sacroiliac dysfunctions, there must be successful fusion between the sacrum and ilium bones at the sacroiliac joint. Fusion of any two bone structures is facilitated by two major factors, namely, stability and compression. Stability refers to elimination or reduction of motion across the surfaces to be fused, and compression enhances stability by creating frictional contact between the surfaces to be fused.

In its simplest form, the device of this invention can be characterized as an elongate implant or body having a hollow core and a plurality of openings or apertures formed in the implant which communicate with the hollow core. The hollow core is of a substantially uniform diameter. This arrangement allows for bony ingrowth through the holes or apertures in the implant to the hollow core which is filled with a substance which encourages bony ingrowth. The implant further includes two sets of threads, one at the proximal end and one at distal end of the device, which causes the opposing bone structures to be brought together in compression. The threads are like-handed, but the distal set of threads has a greater pitch which induces compression forces on the opposing bone structures when the implant is screwed across the joint.

In the preferred embodiment, means are provided on the proximal end of the implant to accommodate a tool which may be used to install the implant. The major diameter of the distal end is smaller than the major diameter of the proximal end so that the cancellous bone on the iliac side of the joint is not disrupted by contact with the distal threads when the implant is being installed. The hollow core of the implant can be filled either with bone graft according to traditional bone graft techniques, or may be filled with substances known as bone morphogenic proteins (BMP). These proteins are produced by genetic engineering techniques and have the property of "turning on" the cellular switch which initiates bone formation. BMP is currently undergoing FDA (Food and Drug Administration) approval for use in the United States. BMP can be adsorbed onto a carrier substance such as a collage sponge which can then be used in lieu of bone graft material. The invention disclosed herein specifically recognizes the ability to use bone graft or carriers soaked with BMP.

The sacroiliac implant of this invention facilitates fusion of the sacroiliac joint by producing stability through its purchase on both the ilium and the sacrum. This purchase is increased cover the use of conventional bone screws by providing a greater total surface area in contact with the cancellous bone in the ilium and in the sacrum. As discussed above, while traditional bone screws may provide surface area contact across a fracture based upon the size of the screw and thread arrangements, such bone screws do not incorporate the attributes of a fusion cage which achieves stabilization between two bone structures by allowing the bones to actually incorporate the cage through bony ingrowth.

Additional advantages of this invention will become apparent from the description that follows, taken in conjunction with the accompanying drawings.

BRIEF DESCRIPTION OF THE DRAWINGS

FIG. 1 is a perspective view, on a greatly enlarged scale, of the sacroiliac implant of this invention, and a fragmentary perspective view of a tool which can be used to install the sacroiliac implant;

FIG. 2 is a vertical section taken along line 2—2 of FIG. 1, and a corresponding fragmentary elevation view of the tool;

FIG. 3 is a plan view of the sacroiliac implant of FIG. 1;

FIG. 4 is an end view taken along line 4—4 of FIG. 1;

FIG. 5 is another end view, but taken along line 5—5 of FIG. 1;

FIG. 6 is an elevational or anterior view of two sacroiliac implants installed across a sacroiliac joint;

FIG. 7 is an enlarged side view of two sacroiliac implants installed across the sacroiliac joint;

FIG. 8 is an enlarged fragmentary perspective view of one sacroiliac implant prior to installation and another sacroiliac implant installed across the sacroiliac joint; and FIG. 9 is a horizontal section taken along line 9—9 of FIG. 8 illustrating two sacroiliac implants after installation.

BEST MODE FOR CARRYING OUT THE INVENTION

The sacroiliac implant 10 of this invention is shown in FIG. 1 as an elongate implant having a proximal threaded section 12, a distal threaded section 14, and an unthreaded intermediate section 16 interconnecting the proximal and distal sections. A plurality of openings or apertures 18 extend from the outer surfaces of the implant to the cylindrical inner surface 20 which defines a hollow core. These openings or apertures 18 provide the conductive pathways by which bony ingrowth is achieved. Proximal threads 22 and distal threads 24 are like-handed, but are of different pitches. "Like-handed" is defined as the extension of the threads in the same angular direction along the longitudinal axis of the implant. In order to achieve compression at the joint, the distal threads 24 have a higher pitch in comparison to the proximal threads 22. In other words, the distal threads 24 make fewer rotations per axial length of the implant as compared to the proximal threads 22. Thus, as shown in FIG. 2, the distal threads 24 are spaced further apart than the proximal threads 22. As best seen in FIGS. 1 and 2, the plurality of openings or apertures 18 are formed in both proximal threads 22 and distal threads 24 of proximal section 12 and distal section 14, respectively. Additionally, intermediate section 16 is shown without any openings 18. Although best results are achieved when openings 18 are formed on both the proximal and distal threaded sections, at least acceptable results can be obtained by providing the openings 18 only on either the proximal or distal threaded sections. Intermediate section 16 is typically unthreaded; however, it may be necessary in some circumstances to allow bony ingrowth at the interface between the two joined bone structures. Accordingly, openings 18 could optionally be provided along intermediate section 16.

The ability of the implant 10 to produce compressive forces on the opposing bone structures across the joint is enhanced by providing radially extending pressure surfaces 26 and 28 of threads 22 and 24, respectively. As shown, these pressure surfaces 26 and 28 extend substantially radially or normal to the longitudinal axis of the implant, and the surfaces 26 and 28 face the intermediate section 16. These radially extending pressure surfaces uniformly distribute the compressive forces to the surrounding bone tissue along the longitudinal axis of the device. Threads 22 and 24 also have opposing or banking surfaces 30 and 32, respectively, which are angled relatively acute to the longitudinal axis. As shown, these banking surfaces 30 and 32 face in opposite directions to one another.

As also shown in FIG. 2, the radial depth of distal threads 24 may slightly exceed that of proximal threads 22. Since threads 24 are arranged at a higher pitch, there are fewer effective threads per unit length. Accordingly, in order to make the compressive surface areas comparatively equal between the proximal and distal threads, the radial depth is increased for the distal threads. However, it shall be understood by those skilled in the art that the particular pitch and radial depth of both the distal and proximal threads may be adjusted as necessary to provide the necessary compressive forces to be applied as well as to provide the necessary thread surface area in contact with the bone for stability.

When the implant is screwed or rotatably driven into the joint, the distal section 14 will advance a predetermined amount further than the proximal section 12 which, in turn, causes the sacrum bone and ilium bone to advance toward one another across the joint until they are in contact and in compression. The pitch differential between the proximal and distal threads determines the rate at which the bones are drawn together in compression.

The proximal face 34 may be adapted to receive a driving tool 40. Specifically, diametrically opposed slots 36 may be formed on proximal face 34 and a circumferential channel 38 may be formed on the inner cylindrical surface 20 at the proximal section 12.

The tool 40 has a larger cylindrical section 42 with opposed mating flanges 44 which are sized to engage slots 36. A smaller diameter cylindrical extension 46 extends from larger section 42 and is sized to fit frictionally within the hollow core against inner surface 20. A spring loaded ball detent 48 is disposed on the distal end of extension 46. At the appropriate point in the surgical procedure when the sacroiliac implant is ready to be installed, cylindrical extension 46 is inserted within the hollow core and ball detent 48 resides in circumferential channel 38. Mating flanges 44 are aligned with slots 36 and the sacroiliac implant may then be screwed into place.

As best seen in FIG. 3, the proximal section 12 has the largest thread crest diameter or major diameter shown as diameter a. Section 12 also has a thread base diameter or minor diameter shown as diameter b. The distal section 14 can also be defined as having a thread crest diameter or major diameter shown as diameter c, and a thread base diameter or minor diameter shown as diameter d. The intermediate section 16 is shown as having a diameter which is substantially the same as the thread base diameter d of distal section 14. As also illustrated, both the thread crest diameter a and the thread base diameter b of proximal section 12 exceed the thread crest diameter c of distal section 14.

For purposes of understanding the relative dimensions of the preferred embodiment, acceptable dimensions which could be used for the sacroiliac implant are as follows: the overall length of the implant is approximately 32 mm, the proximal section 12 being 13 mm, the distal section 14 being 15 mm, and the unthreaded intermediate section 16 being 4 mm. The unthreaded portion of the proximal section 12 at the proximal face 34 is approximately 3 mm, and the threaded portion is approximately 10 mm. Diameters a and b are 21 mm and 19 mm, respectively. Diameters c and d are 18 and 15 mm, respectively. Although specific dimensions have been provided, it shall be understood that this invention is not specifically limited thereto, and the dimensions are only provided for purposes of disclosing one example incorporating acceptable relative dimensions. In some circumstances, it may be desirable to make the proximal or distal sections longer or shorter, and it may also be desirable to make these sections larger or smaller in diameter depending upon the patient and the nature of the joint immobilization to be achieved.

FIGS. 4 and 5 are end views illustrating the proximal and distal ends, respectively, of the implant. As shown, the radial thickness of proximal face 34 is wider than that of distal face 35. Also, as shown in FIG. 2, proximal face 34 and distal face 35 extend transversely to the longitudinal axis of the implant.

FIGS. 6–9 illustrate two sacroiliac implants installed across the sacroiliac joint 54. Based upon the dimensions discussed above, use of these sized devices best stabilize the joint when two are used. The sacroiliac is an undulating joint which traverses across many different planes depending upon the angle viewed. FIGS. 8 and 9 best show the two implants installed across the sacroiliac joint 54. As shown, the distal section 14 is secured within the sacrum bone 50 while the proximal section 12 remains secured in the ilium bone 52. In order to better understand the perspective taken in FIGS. 6 and 7, tail bone 56 is also identified, along with hip sockets 58.

The sacroiliac implant of this invention can be made from a variety of materials. One acceptable material is titanium which is highly resistant to corrosion and exhibits excellent biocompatibility.

The brief description which follows explains one minimally invasive surgical technique or procedure by which the sacroiliac implant of this invention may be installed. A patient is positioned prone on an image table. An image intensifier is used to provide clear visualization of the sacroiliac joint in multiple planes. A stab wound incision is made on the buttocks over the targeted area of the sacroiliac joint. A guide wire is positioned percutaneously on the surface of the ilium bone 52 overlying the inferior portion of the sacroiliac joint 54. Progressively larger cannulated dilators are passed over the guide wire until a working sleeve or trochar is docked into position on the ilium bone 52. A reamer is then used to create an open channel across the joint 54 and into the sacrum 50. This first reaming step utilizes a reamer having a diameter to cut a channel which is substantially the same as the minor or thread base diameter d of the distal section 14. An image intensifier as well as an endoscope are used to assess adequate penetration of the reamer across the joint. Cartilage and other tissue within this area of the sacroiliac joint are removed. A tap is used to cut threads on the sacral side of the joint within the channel created by the reamer. The area of the joint which has been cleared of all cartilage and other tissue may be partially filled with pieces of BMP-soaked carriers or bone graft. A larger iliac reamer is then used to create the appropriate sized channel in the ilium 52 in order to receive the proximal section 12. An iliac tap is also used to create threads for this larger channel within the ilium 52. It is also contemplated by this invention that the threads 22 and 24 could be self-tapping. As well understood by those skilled in the art, the threads 22 and 24 could have fluted surfaces which would allow them to cut into the prepared channels as the implant is screwed into place. Prior to inserting the sacroiliac implant within the prepared channels, the hollow core of the implant is filled with either bone graft or a BMP-soaked carrier. By use of the tool 40, the sacroiliac implant may be screwed into position across the sacroiliac joint. As the distal threads 22 engage the bone on the sacral side of the joint, the opposing bone structures are drawn together. The implant is fully seated when the opposing bone structures come into contact. The bone graft or BMP-soaked carrier pieces placed around the joint fill any small gaps remaining between the compressed bones. Alternatively, instead of filling the hollow core of the implant with bone graft or a BMP soaked carrier prior to insertion in the prepared channels, the implant could first be fully seated, and then bone graft or the BMP soaked carrier could be injected under pressure into the hollow core. This in-situ introduction of bone graft or BMP material into the hollow core would have the advantage of also introducing such material directly into the apertures 18, and into any small voids or gaps surrounding the sacroiliac joint. When the sacroiliac implant is seated fully within the prepared channels, the proximal face 34 is slightly countersunk with respect to the exposed surface of the ilium bone 52. This minimizes any interference with the gluteal musculature which eventually heals over the proximal face 34. The working sleeve or trochar is removed and the stab wound incision is closed. A similar procedure may then be carried out for installation of another sacroiliac implant along another area of the sacroiliac joint.

In addition to the minimally invasive endoscopically assisted procedure discussed above, the operation can be accomplished through a more traditional surgical approach which requires a 5" to 8" incision, and requires stripping of the attachment of the portion of the gluteal muscle groups from the ilium. According to this open surgical technique, the sacroiliac joint is viewed directly. Of course, the minimally invasive endoscopically assisted approach has the advantages of producing less scarring, and minimal or no residual weakness in the hip muscular.

By the foregoing, it can be seen that the sacroiliac implant of this invention provides distinct advantages over the prior art. Because of the unique problems associated with symptomatic sacroiliac dysfunction, standard bone screws or fusion cages are by themselves inadequate to provide the necessary compression and fusion to immobilize a joint such as the sacroiliac. With the sacroiliac implant of this invention, excellent stability and compression can be achieved because of the differential thread pitch arrangement. Stability and structural integrity across the joint is also improved through fusion achieved by bony ingrowth through the apertures formed in the exterior surface of the implant. Ultimately, the overall surface area of bone in contact with the implant is increased which better immobilizes the joint.

This invention has been described in detail with reference to a particular embodiment thereof, but it will be understood that various other modifications can be effected within the spirit and scope of this invention.

What is claimed is:

1. An implant for immobilizing a joint between opposing bone structures, said implant comprising:
   a cylindrical proximal section having, a first outer diameter, and a first uniform helical thread having a first pitch;
   a cylindrical distal section having a second smaller outer diameter and a second uniform helical thread having a second pitch which is greater than said first pitch;
   an intermediate section interconnecting said proximal section and said distal section;
   said proximal, distal and intermediate sections having a contiguous interior surface defining a hollow core;
   at least one of said proximal and distal sections having a plurality of openings extending radially from and in communication with said hollow core and aligned transversely to a longitudinal axis of said implant; and
   means on said proximal section for accommodating a tool to drive said implant.

2. An implant, as claimed in claim 1, wherein:
   said first and second threads each have radially extending surfaces facing said intermediate section for applying forces against said bone structures to cause said bone structures to be drawn together in compression.

3. An implant, as claimed in claim 1, wherein:
   said first and second threads each have respective radial depths, and said second thread has a radial depth which is greater than a radial depth of said first thread.

4. An implant, as claimed in claim 1, wherein said means for accommodating comprises:
   a slot formed on said proximal section.

5. An implant, as claimed in claim 4, wherein said means for accommodating further comprises:
   a circumferential channel formed on said interior surface at said proximal section.

6. An implant, as claimed in claim 1, wherein:
   said proximal and distal sections are axially longer than said intermediate section.

7. An implant, as claimed in claim 1, wherein:
   said distal section is axially longer than said proximal section.

8. An implant, as claimed in claim 1, wherein:
   said hollow core has a substantially uniform diameter.

9. An implant, as claimed in claim 1, further including:
   a bone producing material selected from the group consisting of a bone graft or a bone morphogenic substance, positioned inside said hollow core.

10. An implant, as claimed in claim 1, wherein:
    said proximal and distal sections have a plurality of said openings extending therethrough.

11. An implant for immobilizing a joint between opposing bone structures, said implant comprising:
    a body extending along a longitudinal axis and having proximal and distal sections, an intermediate section interconnecting said proximal and distal sections, a hollow core formed along said longitudinal axis, and a plurality of openings formed through said body in communication with said hollow core and extending transversely to said longitudinal axis;
    a first set of threads formed on said proximal section having a first uniform pitch and a thread crest defining a first larger diameter; and
    a second set of threads formed on said distal section having a second greater uniform pitch, and a thread crest de fining a second smaller diameter.

12. An implant, as claimed in claim 11, wherein:
    said intermediate section is unthreaded.

13. An implant, as claimed in claim 11, wherein:
    said first and second threads each have radially extending surfaces facing said intermediate section for applying forces against said bone structures to cause said bone structures to be drawn together in compression.

14. An implant, as claimed in claim 11, wherein:
    said first and second sets of threads each have respective radial depths, and said second set of threads has a radial depth which is greater than a radial depth of said first set of threads.

15. An implant, as claimed in claim 11, further including:
    means on said proximal section for accommodating a tool to drive said implant.

16. An implant, as claimed in claim 11, wherein:
    said hollow core has a substantially uniform diameter.

17. An implant, as claimed in claim 11, further including:
    a bone producing material selected from the group consisting of a bone graft or a bone morphogenic substance, which is placed inside said hollow core.

18. An implant for immobilizing a joint between opposing bone structures, said implant comprising:
    means for producing compression between the opposing bone structures across the joint, said means for producing compression comprising dissimilarly pitched, externally threaded sections of said implant;
    means for allowing bony ingrowth to occur through said implant to help fuse said bone structures, said means for allowing formed integrally with said means for producing compression;

a bone producing material placed inside a hollow core of said implant, and said material being selected from the group consisting of a bone graft or a bone morphogenic substance; and means on said implant for accommodating a tool to drive said implant.

19. An implant, as claimed in claim 17, wherein:

at least a portion of said means for allowing bony ingrowth extends through at least a portion of said means for producing compression.

* * * * *